United States Patent [19]
Axelgaard

[11] Patent Number: 5,450,845
[45] Date of Patent: Sep. 19, 1995

[54] MEDICAL ELECTRODE SYSTEM

[76] Inventor: Jens Axelgaard, 811 Tumbleweed La., Fallbrook, Calif. 92028

[21] Appl. No.: 3,120

[22] Filed: Jan. 11, 1993

[51] Int. Cl.⁶ .................... A61B 5/04; A61N 1/04
[52] U.S. Cl. ............................. 128/640; 604/20; 607/149; 607/152; 607/153
[58] Field of Search ..................... 128/639–641; 607/149, 152, 153; 604/20

[56] References Cited

U.S. PATENT DOCUMENTS

| | | | |
|---|---|---|---|
| 4,633,879 | 1/1987 | Ong | 128/641 |
| 4,635,641 | 1/1987 | Hoffman | 128/641 |
| 4,708,149 | 11/1987 | Axelgaard | 128/798 |
| 4,722,354 | 2/1988 | Axelgaard | 128/798 |
| 4,763,660 | 8/1988 | Kroll et al. | 128/640 |
| 4,820,263 | 4/1989 | Spevak et al. | 607/149 X |
| 4,989,607 | 2/1991 | Keusch | 128/640 |
| 5,069,908 | 12/1991 | Henly | 421/449 |
| 5,265,579 | 11/1993 | Ferrari | 128/640 |

FOREIGN PATENT DOCUMENTS 2240928  8/1991  United Kingdom ........... 128/641

Primary Examiner—Lee S. Cohen
Attorney, Agent, or Firm—Walter A. Hackler

[57] ABSTRACT

A medical electrode system includes an electrically non-conductive backing material and a flexible, electrically conductive patch disposed on the backing material. An electrically non-conductive facing material is disposed over the patch which includes an aperture therein for exposing a portion of the patch, said aperture having a maximum dimension smaller than a minimum dimension of the patch. A lead wire electrically connected to the patch, and a separate electrically conductive gel pad is provided for releasably coupling the patch to a body part, the gel pad having a minimum dimension larger than the aperture's maximum dimension and formed from a material enabling the gel means to be removed, intact, from said body part and patch. The gel pad may further include a drug suitable for iontophoretic delivery. A strap system enables the patches and backing material to be applied in a compressing manner on a body part and in one embodiment, the entire system is both stretchable and flexible.

29 Claims, 4 Drawing Sheets

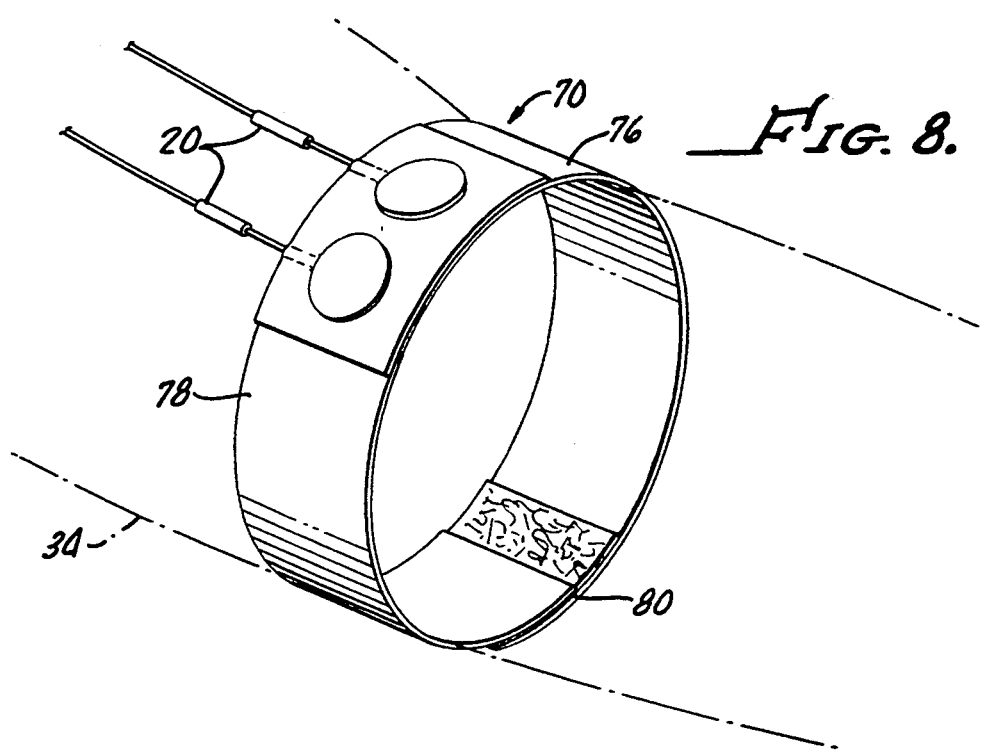
FIG. 8.
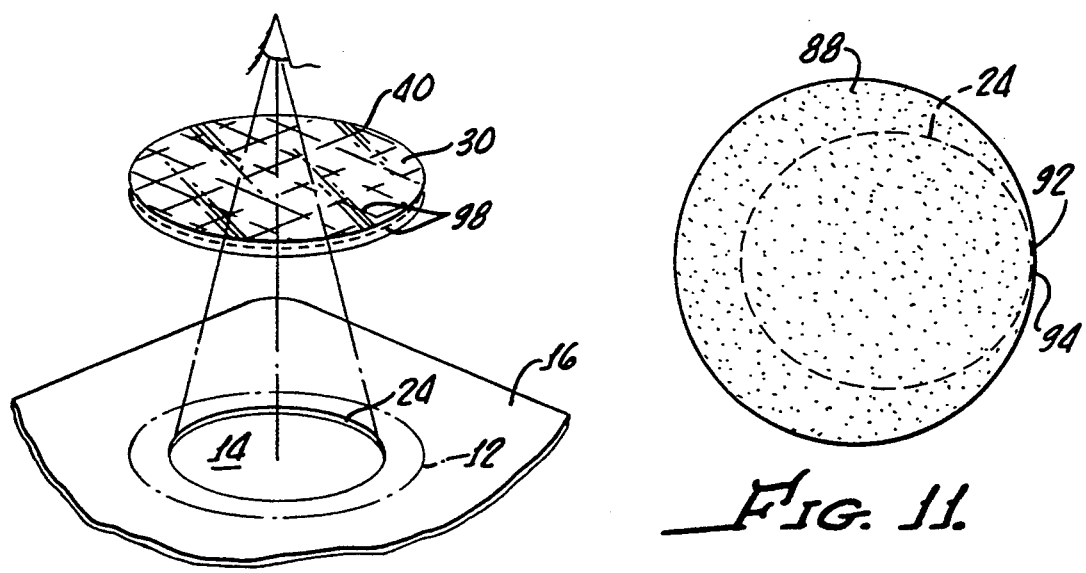
FIG. 9.
FIG. 11.
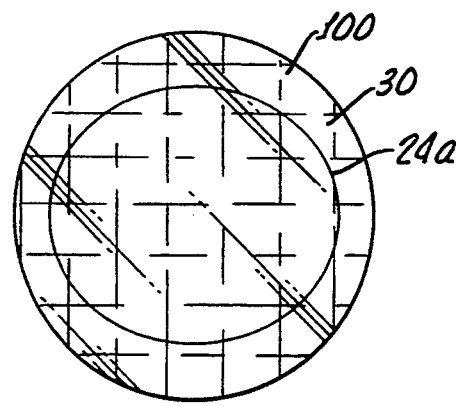
FIG. 10.

MEDICAL ELECTRODE SYSTEM

The present invention generally relates to electrode systems and more particularly to a medical electrode system having utility for obtaining desired physiologic responses for the assessment or treatment of diseases and injuries in humans. This includes the sensing of electrical signals, for electrograph (EKG), electroencephalograph (EEG) and electromyograph (EMG) devices, and emitting electrical pulses for transcutaneous electrical devices, such as transcutaneous electrical nerve stimulation (TENS), electrical muscle stimulation (EMS), neuromuscular stimulation (NMS) and functional electrical stimulation (FES), as well as interferential and iontophoresis therapy.

In general, monitoring electrodes for EKG, EEG and EMG devices are generally small since a relatively small contact with a skin surface is sufficient for reception of electrical signals.

On the other hand, stimulation electrodes for TENS, EMS, interferential and iontophoresis devices generally require a larger skin surface contact in order to provide sufficient transcutaneous electrical current to effect a desired physiologic response.

More particularly, electrode systems suitable for use in nerve and muscle stimulation must, of course, provide sufficient electrical potential in order to conduct appropriate current against the impedance of the conductive medium. In this regard, electrical stimulators are designed as either constant-current or constant-voltage stimulators.

It has been found that basic physiologic responses and clinical results are usually identical, whether constant-voltage or constant-current stimulators are used; however, the advantage of constant-voltage devices is the automatic reduction of current when electrode size is reduced or if electrode contact with the skin becomes loose. On the other hand, if pressure between tissue and the electrode is suddenly increased, impedance is reduced, and current intensity is automatically increased, thus intensifying the stimulation level.

The advantage of constant current devices is a consistent level of stimulation, but this may not occur when electrode size or pressure with the skin or both are reduced, leading to a sudden increase of stimulation voltage. Thus, suitable electrodes are those which provide uniform electrical coupling across the skin for proper electrical interfacing.

The history of muscle and nerve stimulation therapy has included a number of electrodes utilizing a variety of conductive elements, including carbon impregnated rubber, as well as metallic foils and wet sponges.

Many of the early prior art devices are lacking in flexibility and this deficiency has resulted in the abandonment of many of the earlier electrode systems. Thus, any successful electrode device must be sufficiently flexible in order to accommodate the curvaceous nature of the human body and also to accommodate relative movement of the patient's skin therebeneath during therapy, since nerve and/or muscle stimulation may cause muscle contraction and concomitant skin movement, as occurs in EMS.

During long periods of therapy, perspiration from the skin may cause loosening or disruption of the electrode position on the skin. Naturally, this condition is directly associated with electrode size, with the larger the electrode, the longer the evaporation path, or distance, perspiration, occurring at the center regions of the electrode, must travel in order to evaporate, or be released to the atmosphere.

It has also been experienced with prior art electrodes that a simple compression systems utilizing medical adhesive tape, or the like, have a tendency to lift from the skin because of perspiration and movement of the patient's skin during treatment.

The simple holding of a medical electrode on to the skin may not provide suitable electrical contact either for EKG, EEG and EMG applications, and for TENS, EMS and FES applications.

As hereinabove noted, nerve and stimulation therapy may be utilized over long periods of time, and this is particularly true in connection with sports injuries. It has been experienced that insufficient flexing of an electrode system can result in severe irritation of the patient's skin in electrical "hot spots" due to uneven electrical-skin contact which manifests itself in a rash and a burning sensation.

In view of the electrical coupling problems, workers have most recently turned to conductive electrolytes, in the form of fluids and gels, to provide sufficient electrical coupling between the electrode and the skin.

One type of electrode utilized for temporary application of muscle stimulation electrodes includes a flat, smooth contacting surface and a separate conductive cream or gel applied to the skin to electrically couple the electrode thereto. Experience with this system has shown that the cream or gel is messy to use and remove and that the electrodes are not suitable for curved body parts. After use, the cream or gel must be cleaned or washed from the skin and electrode. Also, uneven application of the gel may create "hot" spots of high current density leading to skin burns.

Another type of electrode most suitable for long term application of electrical stimulation for monitoring electrodes includes a flexible conductive fabric or material. Generally, this type of electrode includes an electrically conductive woven, knit or mesh material, with a gel electrolyte impregnated therein in order to improve electrical conduction within the electrode.

Conductive gels have been developed which are adhesive so that they perform a dual function by both electrically coupling the electrode to the body and adhering the electrode to the body. A typical electrode of this type is disclosed in U.S. Pat. Nos. 4,708,149 and 4,722,354. These electrodes include a conductive fabric with a flexible conductive adhesive disposed on a side of the conductive fabric for adhering the flexible transcutaneous electrical nerve and/or muscle stimulation electrode to the skin of a patient. While this type of electrode is effective, a great number of electrodes may be required to provide long term treatment for certain injuries, such as those incurred in sports.

Since most of the known electrode systems are disposable in nature and useful only for relatively short periods of time, due to removal for body hygiene, a considerable expense may be anticipated in the treatment of a patient undergoing long term therapy.

An important aspect of electrode stimulation pertains to appropriate electrode placement. In this regard, two basic techniques are utilized: monopolar and bipolar.

In the monopolar technique, only one of two electrodes is placed over a target area to be treated. This electrode has been conventionally identified as a treatment, or stimulating electrode. Another non-treatment or dispersive electrode is disposed over an area that is not to be treated by stimulation. The target area may include a muscle, joints, bursae, hematomas, dermal ulcers, as well as trigger and acupuncture points, depending on the clinical problem and its appropriate treatment procedure.

The nontreatment electrode is commonly known as the dispersive electrode because it is usually, though not always, a large electrode. Large size minimizes current density, thereby preventing current from being perceived under it. If the treatment electrode is very small, then the nontreatment electrode need be only somewhat larger. The treatment electrode may be one or more electrodes.

In the bipolar technique, two electrodes are placed over or adjacent a target area to be treated. In this manner, the conductive current and current flow are confined to the target area. In contrast to the monopolar technique, excitatory responses are perceived under both electrodes of the circuit. Obviously, the two electrodes are usually, but not necessarily, of the same size, and the nontreatment, dispersive electrode is not used.

Bipolar placement of the electrodes can be used with any TENS, or EMS, including high-voltage stimulation, and the current may be pulsation, monophasic, biphasic or polyphasic.

Modern stimulation utilizes two or more channels or electrical outputs. When two channels are used simultaneously over the same target area, each channel may be arranged in a bipolar placement technique. The dual-channel arrangement, however, can take several configurations in order to improve pain relief.

In one configuration, one channel provides electrical output to two separate electrodes disposed on one side of a target area while a second channel provides electrical power to two separate electrodes disposed on another side of the target area. This is known as the bracket method.

In another configuration, one channel provides electrical output to a first pair of separate electrodes, each disposed on opposite sides of a target area while another channel provides electrical output to a second pair of electrodes, each disposed on opposite sides of the target area and adjacent to the first pair of electrodes. This is known as the criss-cross method. If an interferential stimulator is connected to this electrode layout, a low-frequency interference frequency between two high-frequency currents of each channel provides therapeutic deep tissue penetration.

Interferential stimulators utilize two sinusoidal current sources that differ somewhat from one another in frequency. When these two outputs intersect, the difference in frequency causes the pulse intensities to be combined, resulting in a so-called beat or envelope-shaped pulse. Each such beat actually represents a single polyphasic pulse and each polyphasic pulses acts in a fashion similar to the single monophasic or biphasic pulse of a conventional TENS stimulator.

This multiple electrode approach may be used in cases where a painful target area or the desired ipsilateral stimulation points are hyperesthetic or irritable, such as postherpetic neuralgia, causalgia, and reflex-sympathetic dystrophy.

Changing to another field in the area of clinical electrotherapy, the present invention also finds utility in the field of iontophoresis, as earlier noted.

Iontophoresis utilizes an electrical electrode to provide an electric field in order to cause interaction between ionized molecules of a drug which results in the migration of the ionized molecules through the skin.

Heretofore, this migration has been achieved by placing two electrodes on a patient's skin which are connected to an electrical power supply, with one of the electrodes being filled with a drug solution, and the other electrode filled with an electrolyte solution. As is well known, an electric field generated between the electrodes causes charged drug molecules to move, or migrate, from the drug containing the electrode through the skin of a patient.

The advantages of iontophoresis are many-fold and include the avoidance of hypodermic injection and further avoidance of possible metabolism of the drug when it is orally administered.

That is, when a drug is taken orally and absorbed from the digestive track into the blood stream, the blood containing the drug first passes through the metabolically active liver before it is delivered to the desired target tissue. Hence, a large amount of an orally ingested drug may be metabolically inactivated before it has a chance to exert its pharmacological effect. All of these effects are well known.

Any electrode suitable for iontophoresis also should be of significant size in order to provide adequate conductive surface to prevent burning of the patient's skin during drug transmission. In this regard, the size of the electrode is more comparable as TENS, EMS, and FES electrode as opposed to an EKG, EEG and EMG electrode.

In connection with such electrodes, the device preferably should hold a volume of drug sufficient for an individual treatment session.

Early iontophoresic devices utilized an electrode having a reservoir for holding the drug, or active agent. Naturally, such electrodes are relatively expensive to manufacture and consequently, due to the fact that such electrodes are typically discarded after a single treatment, such systems are expensive.

Recent developments in the field of conductive gels useful for transdermal drug application, have included chemically cross-linked hydrogels which retain an inactive ingredient in prolonged contact with the skin for enhanced drug applications, see U.S. Pat. No. 5,069,908 issued Dec. 3, 1991. These types of hydrogels may be incorporated into iontophoresis electrodes in a manner described in U.S. Pat. No. 4,708,149 and 4,722,354 hereinabove discussed.

In all of the applications which the present invention finds utility, the control of current distribution is of utmost importance. When the current distribution is properly controlled, a comfortably transition between stimulated and non-stimulated areas, allows a patient to tolerate higher voltages and currents which results for not only a better therapeutic effect, but for a greater transference of an active agent through the skin.

The present invention is directed to a medical electrode system in which the basic electroconducting and electrical distribution portion of the electrode is reusable and, in fact, washable.

In combination therewith, and in accordance with the present invention, a separate adhesive electrical conductive pad is used to couple the "dry" electrode to the skin. Thus, only an expendable gel pad material need be disposable throughout the treatment of the patient. This is particularly important in the field of iontophoresis. In this regard, the electrode may be reused, while only the drug containing conductive adhesive is disposed. Further, the same drug laden gel adhesive pad may be utilized to deliver various different doses depending upon the electrode configuration.

In addition, one embodiment of the invention also utilizes a plurality of electrodes and a system of insuring proper placement of the electrode set on the body part.

SUMMARY OF THE INVENTION

In accordance with the present invention, a medical electrode system generally includes an electrically nonconductive backing material and a flexible electrically conductive patch disposed on the backing material.

In addition, an electrically non-conductive facing material is disposed over the patch with the facing material including means, defining an aperture therein, for exposing a portion of the patch. In this embodiment, the aperture has a maximum dimension smaller than a minimum dimension of the patch.

A lead wire is electrically connected to the patch for providing electrical current thereto for TENS, EMS, and FES devices, or for receiving electrical impulses in the case of EKG, EEG, and EMG devices.

Importantly, a separate electrically conductive gel is provided for releasably coupling the patch to a body part. The gel has a minimum dimension larger than the aperture maximum dimension and is formed from a material enabling the gel to be removed, intact, from the body part and patch. In this manner, the separate electrically conductive gel is the only disposable portion in the present system.

Further, the gel, in accordance with the present invention, may be sufficiently transparent for enabling visual alignment therethrough to facilitate positioning of the gel over the aperture. This is important in ensuring the proper current distribution provided by the electrode system. By providing a visual acuity through the gel when the latter is applied over the aperture, proper centering or coaxial alignment of the gel and the aperture may be affected.

Various distribution patterns may be achieved by varying the relative geometric shape of the patch, the aperture and the gel, with one embodiment of the invention having a circular shape for the patch, aperture and gel.

In one embodiment of the present invention, the backing sheet includes an opening therein for facilitating placement of the backing sheet onto a body part by visually observing the body part through the opening. This feature of the present invention is particularly important when a plurality of flexible electrically conductive patches are disposed on the backing material in a selected array.

The array is selected for enabling coordinated placement of the patches on a selected boy part for specific treatment. Hence, the opening in the backing sheet then enables proper placement of the array of electrodes on a body part for providing proper muscle and/or nerve stimulation or signal recording or signal receiving.

It is well known in the art, that in many instances a plurality of interacting electrodes is most suitable for providing proper muscle stimulation therapy. Unfortunately, if the array of electrodes is not properly disposed on the body part, the synergistic effect of the electrode system is not utilized.

Hence, the electrical patch array in the present electrode system, along with the means for facilitating placement of the system, ensures correct placement of multiple electrical patches for effecting optimum stimulation.

In another embodiment of the present invention, the backing material may not be continuous and in this instance, the facing material may include means defining an opening therein for facilitating placement of the electrode onto a body part by visually observing the body part through the opening.

Alternatively, the backing material and the facing material may be fabric and may comprise a woven fabric with a weave enabling visual acuity therethrough sufficient to facilitate placement of the backing material onto the body part. This embodiment of the present invention functions in a manner to the embodiment hereinabove described without the necessity of a separate opening through the backing or facing material.

In another embodiment of the present invention, means may be provided for enabling the backing material to be applied in a compressing manner on the body part. This embodiment is particularly useful in combination with hot or cold packs for therapeutic treatment and the medical electrode system so utilized may further comprise a moisture barrier disposed between the patch and the backing material. It is common practice in physical therapy and sports medicine to treat and manage soft tissue injuries, such as strains, sprains, contusions and edemas with the ICE method (I=Ice, C=Compression, E=Elevation). Recent research shows that elevation can be substituted for Electrical stimulation accelerating the healing process and simultaneously allowing the patient mobility.

Further, means may be provided for controlling the current distribution provided to the body part from the patch through the gel. This means may comprise and electrically non-conductive facing material disposed over the patch which includes the aperture having various dimensions. By a change of the aperture size and shape, various current distributions may be provided through the gel.

A further embodiment of the present invention includes a separate electrically conductive gel for releasably coupling the patch to a body part and including a drug for iontophoretic delivery into the body part. As hereinabove described, this gel may be formed from a material enabling the gel to be removed, intact from the body part and patch.

In this embodiment, the amount of drug delivered may be controlled in a number of ways. First, the size of the aperture and the facing material may be adjusted; second, the amount of drug in the gel may be varied and further, the electrical current distribution through the gel may be controlled to effect a predetermined amount of drug to be transdermally delivered.

BRIEF DESCRIPTION OF THE DRAWINGS

The advantages and features of the present invention will be better understood by the following description drawings in which:

FIG. 8 is yet another embodiment of the invention utilizing two electrode patches and a Velcro-type strap system for enabling the medical electrode to be applied in a compressing manner on the body part;

FIG. 9 is a perspective view illustrating a feature of the present invention which utilizes a transparent gel for enabling visual placement of the gel over an aperture in the backing material;

FIG. 10 illustrates proper placement of the gel material over the aperture as facilitated by the present invention;

FIG. 11 illustrates a problem associated with opaque gels, which can result in improper placement of the gel over the aperture.

DETAILED DESCRIPTION

Figure 1:
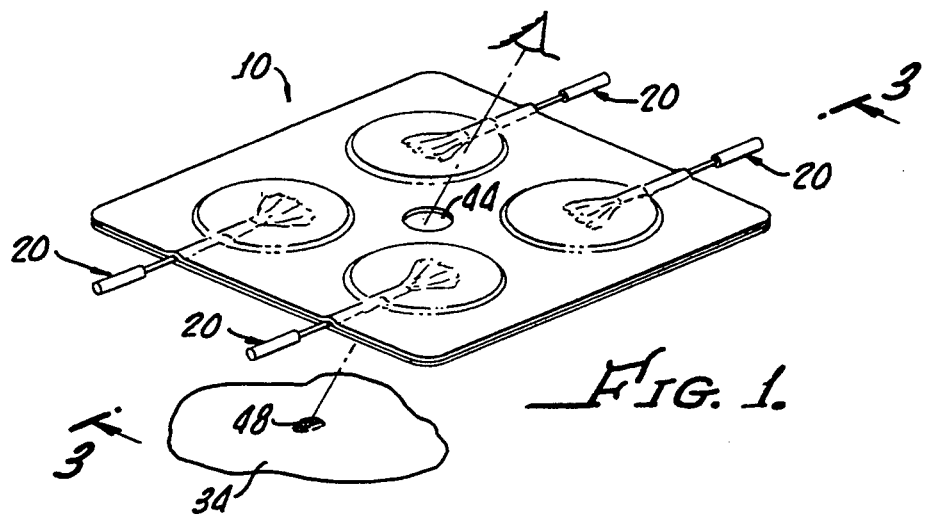
FIG. 1 is a perspective view of a medical electrode system in accordance with one embodiment of the present invention, illustrating means incorporated into the present invention for facilitating placement of the electrode system onto a body part.
Figure 2:
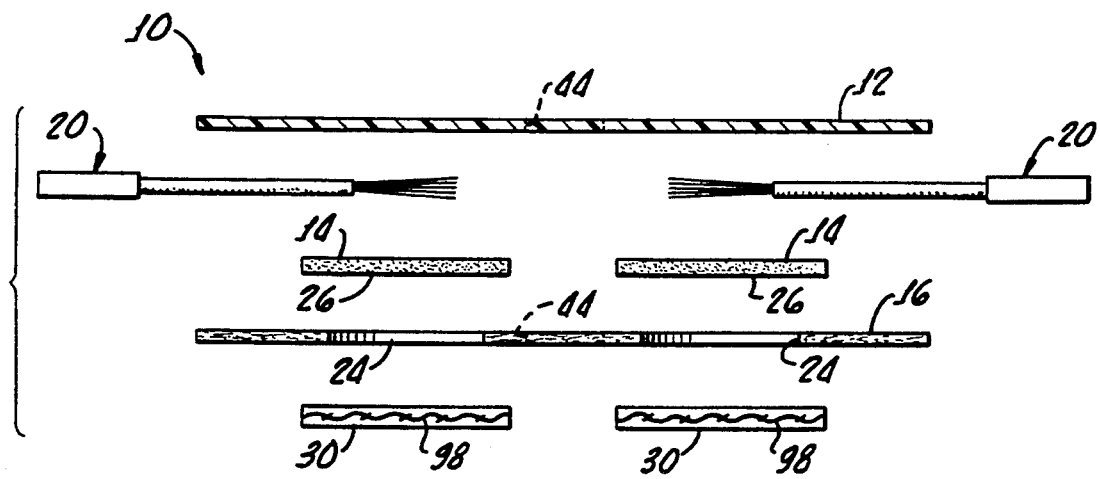
FIG. 2 is an exploded view of the medical electrode system shown in FIG. 1, generally showing an electrically nonconductive backing material, a flexible, electrically conductive patch disposed on the backing material and an electrically nonconductive facing material disposed over the patch along with the lead wire electrically connected to the patch and separate electrically conductive gel means.
Figure 3:
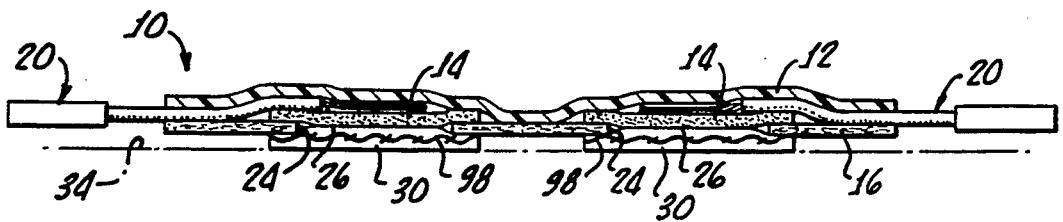
FIG. 3 is a cross-sectional view of the medical electrode system shown in FIG. 1, taken along the line 3—3.

Turning now to FIGS. 1-3, there is shown a medical electrode system 10 in accordance with the present invention generally including a non-conductive backing material 12, a plurality of flexible electrically conductive patches 14 disposed on the backing material 12, and an electrically non-conductive facing material 16 disposed over the patches 14.

It should be appreciated that while four patches are illustrated in FIGS. 1 through 3, for the purpose of interferential therapy, a single or any number of patches may be utilized depending upon the treatment anticipated.

The backing material 12 may be any suitable non-conductive material, including plastic films or woven materials, having suitable flexibility for enabling the electrode system 10 to be disposed on a curved body portion necessary. The flexible, electrically conductive patches 14 may be any suitable conductive fabric such as knit or woven fabrics suitable for electrodes such as described in U.S. Pat. No. 4,722,354, which is incorporated herewith entirely by this specific reference thereto.

Turning to FIG. 2, lead wires 20 may be electrically connected to the patches 14 by compression (glue, ultrasonic welding or other bonding method) between the patches 14 and the backing material 12. Alternatively, the lead wires 20 may be intermeshed with the patches 14, with the patches 14 being attached to the backing material 12 in any suitable manner such as adhesive, for sewing onto the facing material 16.

As hereinabove noted, while a plurality of conductive fabric patches 14 are shown in FIGS. 1-3, a single patch may be utilized depending upon the circumstances of treatment. The array of patches shown in FIGS. 1-3 is only representative in nature; however, it is important to note that the fixing of a conductive fabric patch 14 to the nonconductive fabric 12 overcomes the problem associated with using multiple sets of electrodes. A spaced-apart, fixing positioning of the electrodes, eliminates the cumbersome and unwieldly necessity of separate attachment of electrodes to a body. In addition, with single or smaller sets of electrodes, migration during prolonged stimulation or monitoring may occur and thus cause difficulty in ensuring consistent placement of the electrodes with respect to one another.

This is important, particularly with the placement of monitoring electrodes where the visual display of a patient's heart condition may be distorted through the improper placement of the monitoring electrodes.

More particularly, the nonconductive fabric 12 in accordance with the present invention, as hereinabove noted, may be formed from any suitable material, but is preferably machine-washable. The function of the nonconductive backing material 12 is to provide a support for the conductive patches 14 and, at the same time, prevent any unwanted electrical communication between the electrodes or contact with the electrodes, when the patches 14 are placed in contact with a body 34.

Referring to FIG. 2, the facing material 16 includes a plurality of windows, or apertures 24, for exposing a portion 26 of the patches 14, with the apertures 24 having a maximum dimension smaller than a minimum dimension of the patches 14.

Separate electrically conductive gel pads 30 provide a means for releasably coupling the patches 14 to a body part, or target area, 34. In order to completely cover the windows, or apertures, 24, the gel pads should have a minimum dimension larger than the windows maximum dimension. As long as the windows 24 are covered, there is no risk of direct stimulation from the electrode edges.

Further, this provides a current distribution, as hereinafter discussed in greater detail, which is even across the window 24 and rolls off smoothly over the portion of the gel pads 30 exceeding beyond the window. This occurs because electrical current travels longitudinally in the gel which has an aperture between that of the electrode and the body 34. The net effect is a comfortable transition between stimulated and non-stimulated areas, allowing patients to tolerate higher amplitude settings, often for better therapeutic effects.

The use of a separate gel pad in accordance with the present invention results in a number of advantages heretofore unavailable to unitary medical electrode devices.

First, current distribution may be controlled by utilizing separate gel pads 30 of different conductivity. In fact, when a plurality of patches 14 are utilized, the corresponding gel pads 30 may have different conductivities. Suitable gel pads may be made in accordance with the specification set forth in U.S. Pat. No. 4,989,607, which is incorporated herewith entirely by this specific reference thereto.

While conductive adhesive gel configurations have been known for sometime, as evidenced by the hereinabove referenced patent, they have not been utilized as a separate entity in combination with one or more conductive electric patches as encompassed by the present invention. The electric patches are generally referred to herein with the character reference 14 and individually referred to with the character references 14a, 14b, 14c, and 14d.

It should be clear that by varying the conductivity of individual gel pads 30, different current distributions may be provided with the same electrical input to the electric patches 14. Conversely, the electrical load provided to the patches 14 may be adjusted to accommodate four different conductivities of gel pads 30.

In accordance with the present invention, the gel pad may have an overall thickness of between about half a millimeter and two and one-half millimeters. This thickness ensures that the pad maintains physical integrity so that it may be removed from the patch 14 and the target area 34 in one piece, i.e., intact.

The second feature of the separate pad, importantly, enables the patches 14 and facing material 16 to be removed from the gel pads 30, thereby facilitating reuse of the patches 14 without the necessity of scraping or removal of gel pads 30 therefrom. In addition, in prolonged use, as hereinabove mentioned, the patches 14, backing material 12 and facing material 16, may be washed as necessary between use.

Figure 5:
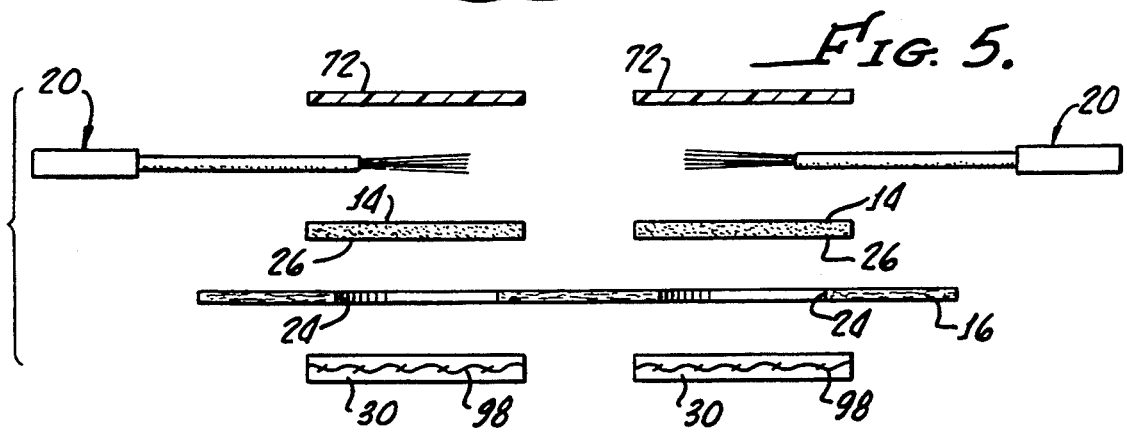
FIG. 5 is an exploded view of the medical electrode shown in FIG. 4.

A further advantage of the separate gel pad 30 is manifest when the gel pad 30 incorporates an active drug, as illustrated in FIG. 5 as particle 40.

In this embodiment, the separate electrically conductive gel pads 30 not only provide a means for releasably coupling the patches 14 to a body part 34, but also, importantly, iontophoretically delivering the drug 40 into the body 34 during applied electrical potential to the gel pads 30.

Most electrically charged drugs are suitable for such delivery and incorporation of such drugs into a gel is described in U.S. Pat. No. 5,069,908, which is incorporated entirely herewith by specific reference thereto.

It can be seen that the use of separate gel patches 30, each including various amounts of drug disposed therein, may be used to effect a wide range of drug delivery requirements. This, effect, of course, is in concert with the electrical potential applied to the electrode.

Thus, the combination of the present invention enables a tailored prescription of dose and dose rate through various gel drug concentrations and different electrical potentials than heretofore has been possible through the use of unitary iontophoretic electrode systems.

Turning again for FIG. 1, an additional feature of the present invention is provided by an opening 44 in the backing material 12 and facing material 16 which provides a means for visually observing the body part through the opening 44, thereby facilitating placement of the backing material 12 and electrode system 10 onto the target area 34.

As hereinabove discussed, the criticality of proper placement of the electrode system, particularly with a selected array of patches 14, is important in therapeutic treatment.

As represented in FIG. 1, this problem is eliminated by the present invention which, as represented, allows observation of a mark 48 on the body 34 through the opening 44. The electrode array shown in FIG. 1, may be connected to a stimulator (not shown) in a bracket or criss-cross manner. In the bracket manner, one channel of a stimulator (not shown) is connected to patches 14a, 14b, while another channel is connected to patches 14c, 14d. In the criss-cross manner, one channel of a stimulator (not shown) is connected to patches 14a, 14d, while another channel is connected to patches 14b, 14c.

Figure 4:
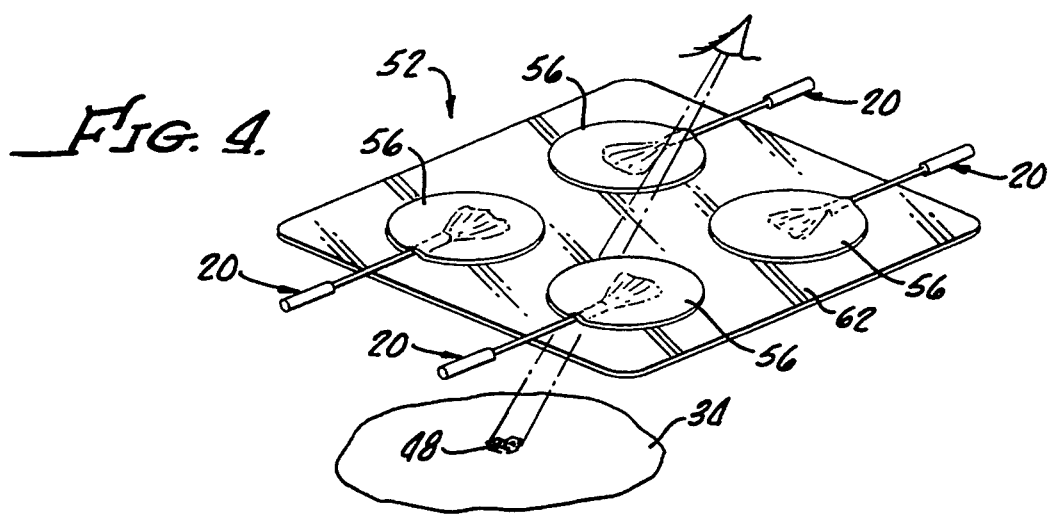
FIG. 4 is an alternative embodiment of the present invention incorporating discrete backing material segments and a transparent facing material for facilitating placement of the medical electrode system to a body part.
Figure 6:
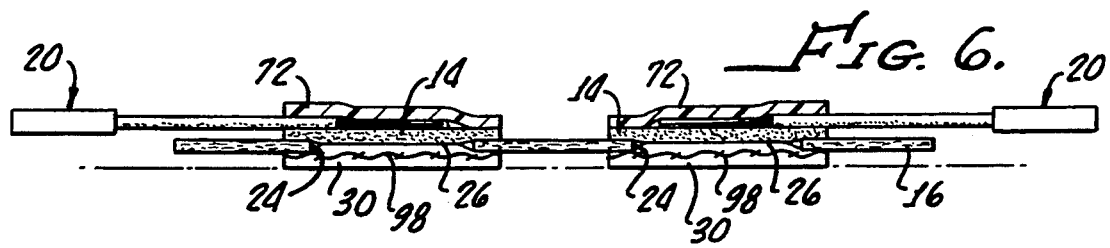
FIG. 6 is a cross-sectional view of the medical electrode shown in FIG. 4, taken along the line 6—6.

An alternative embodiment 52, of the medical electrode system in accordance with the present invention, as shown in FIGS. 4–6, with like elements being referred to by common character references.

The medical electrode system 52 is substantially equivalent to the system 10 shown in FIGS. 1 through 3, except that instead of a continuous backing material 12 (FIGS. 1–3), discrete segments 56 are utilized, which are of larger dimension than the patches 14 in order to prevent electrical contact with the patches 14.

In addition, the facing material 62 is formed from a woven or knit fabric with a weave or knit pattern sufficiently separated to enable visual acuity therethrough in order to facilitate placement of the backing material on to the body part 34. Thus, a mark, or spot 48, may be observed directly through the facing material 62. If a continuous backing material is utilized in this embodiment, then it may also have a sufficiently open weave or a knit, to enable observation of the mark 48 through both the backing and facing material.

Figure 7:
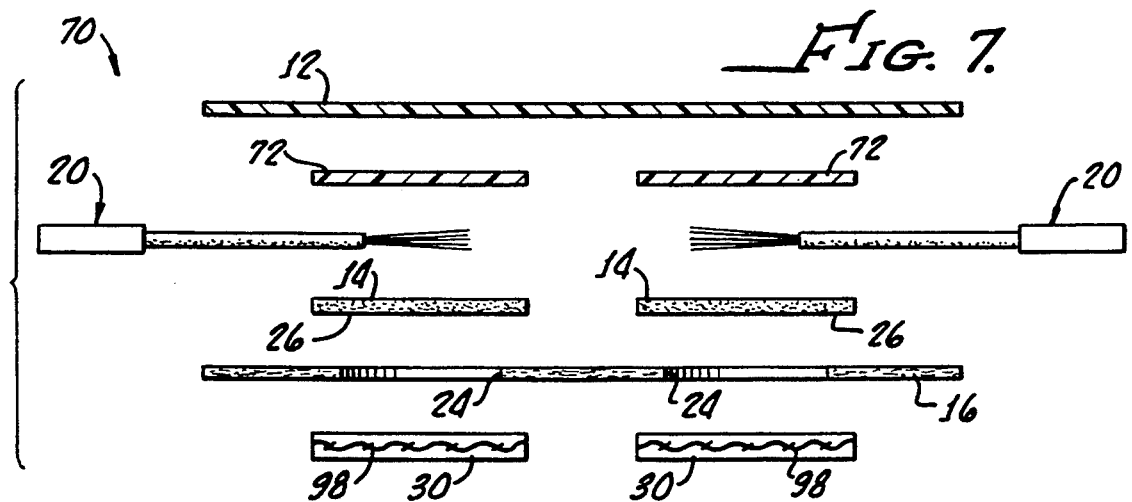
FIG. 7 is an exploded view of another embodiment of the present invention incorporating a separate moisture barrier.

As shown in FIG. 7, a further embodiment 70, in accordance with the present invention, utilizes separate moisture barriers 72, disposed between the patches 14 and the backing material 12. However, it should be appreciated that the backing material itself may be a moisture barrier. Any suitable non-permeable material, such as plastic, may be utilized which is preferably glued in position between the patches 14 and the backing material 12. Other components, or elements of the system 70 shown in FIG. 7, are equivalent to the embodiments 10 and 52, with corresponding elements being referred to by the same reference number or characters.

The embodiments 10, 70, are shown in perspective in FIG. 8 and further includes stretchable straps 76, 78 attached to either side of the backing material 12, which provides means for enabling the medical electrode system 70 to be applied in a compressing manner on the body part 34. The straps 76, 78 may also be extensions of the backing material 12. The straps 76, 78 may be so long as to enable encircling a body member several times like an ACE-bandage.

It is preferable in this embodiment that the backing material 12 be a stretchable material as hereinabove discussed. The strap 76, 78 may preferably by stretchable and joined to one another by a conventional Velcro 80 system. This embodiment further facilitates the use of an ice pack or hot pack 82 in combination with the system, with the barrier 72 preventing moisture from entering the electrode patches 14, which may otherwise occur with the use of ice packs.

The compression applied against the body part 34 may be modified by using various combinations of stretchable backing material 12, patches 14 and straps 76, 78. That is, the backing material, patch 14 and straps 76, 78 may have different stretching characteristics in order to apply a selected compression.

In addition, the cold or hot pack 82 may be wrapped between the straps as the straps 76, 78 are wound around the body part 34 to provide a combined stimulation, heat treatment to a selected body part 34.

Turning now to FIG. 9, there is shown yet another feature of the present invention which ensures proper current distribution through the use or separate gel pads 30 and facing material 16. The gel pads may be formed from a clear gel adhesive, such as available from Promeon of Minneapolis, Minn.

With sufficient transparent gel pads, visual alignment of the gel pads 30 facilitates the positioning of the gel pads over the apertures 24 as shown in FIG. 10. This is important in ensuring uniform electrical conductivity over the patch 14 which is exposed by the aperture 24. Proper alignment is illustrated in FIG. 10 wherein the aperture is clearly visible through the transparent gel, thereby ensuring proper placement of the gel pad over the aperture 24.

As shown in FIG. 11, if an opaque gel pad 88, such as available from Valleylab, Inc., of Boulder, Colo., is utilized, it may be placed over the aperture 24 in a position where edges thereof 92, 94, respectively, approximately coincide. While not observable through the opaque gel pad 88, the proximity of the aperture edge 94 and gel pad edge 92, may cause non-uniform electrical distribution. Naturally, the use of the opaque gel pad 88 is satisfactory in coupling electrical energy from the patch 14 to the body part 34 if properly aligned with the aperture 24.

Alternatively, if the opaque gel 88 is utilized, an outline, or template, in the form of a mark 96 may be made on the substrate 12 in order to facilitate placement of the opaque gel 88. In this instance, the mark 96 should have a radius at least equal to the radius of the opaque gel 88, if round.

Referring again to FIG. 9, a mesh 98 may be disposed within the gel pad 30 for enabling the gel pad 30 to be removed from the body part 34 while maintaining adherence to the patch 14 and facing material 16. This preferential adhesive system is described in copending U.S. patent application Ser. No. 07/887,690 filed on May 21, 1992, now U.S. Pat. No. 5,263,481 and this application is incorporated entirely, including the drawings, by this specific reference thereto.

Again, referring to FIGS. 9 and 10, there is shown non-electrical means for controlling the amount of drug released from the gel pad 30 as well as controlling the current distribution.

These features of the present invention are enabled by electing difference geometric configurations for the patch 14, aperture 24 and gel pad 30. For example, as shown in FIG. 10, an oval aperture 24a, may be used to tailor the current distribution through a circular gel pad 30. In addition, the gel pad conductivity may be varied in order to play a role in determining drug release across the electrode.

Figure 12:
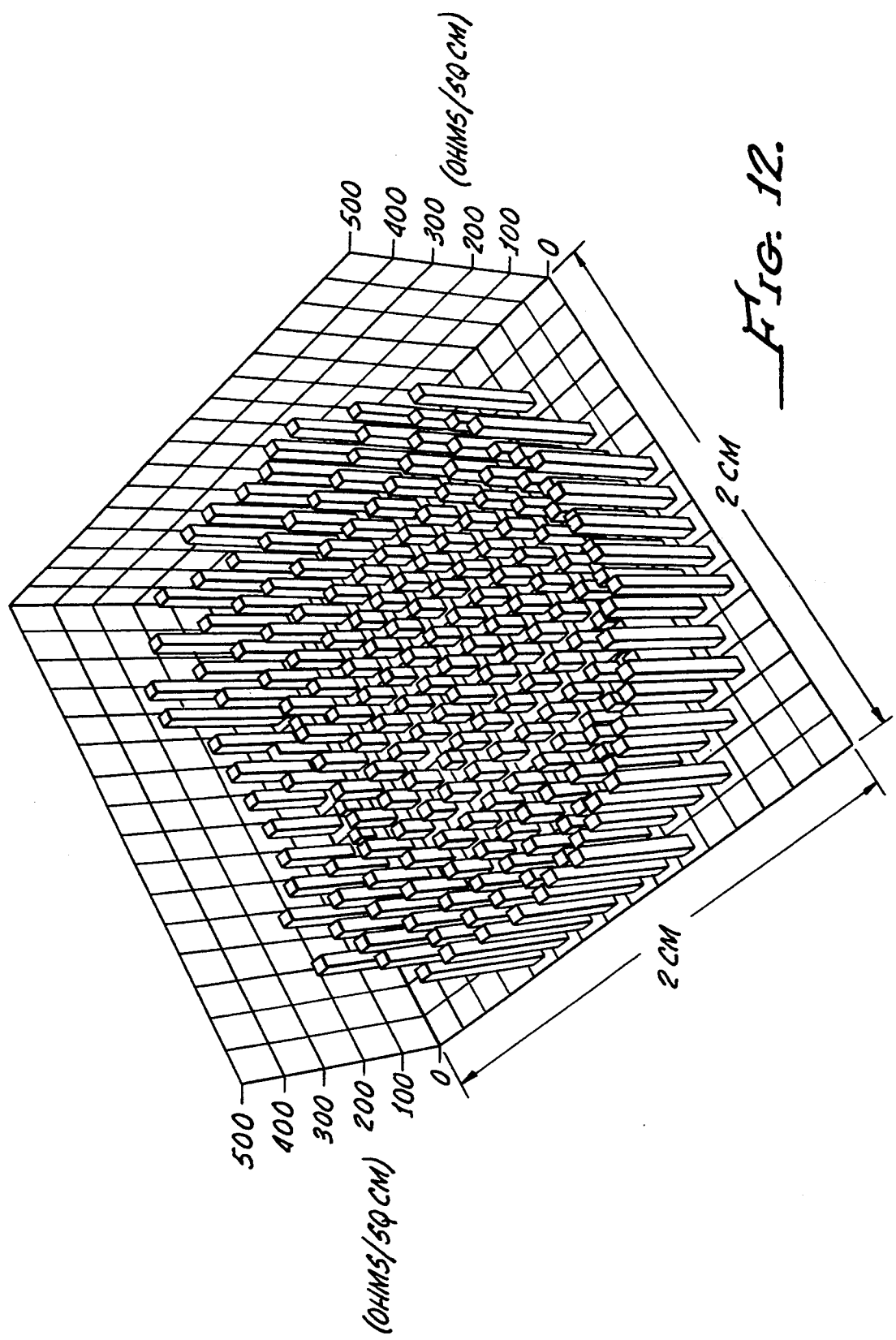
FIG. 12 is a plot of impedance measurements taken across the gel of the present invention when it is disposed over the aperture.

As hereinabove noted, current distribution is even across the window 24, where the current traverses the gel, and rolls off in a gradual manner (see FIG. 12) over the portion 100 of the gel, extending beyond the window, or aperture 24, 24a. The current distribution as shown in FIG. 12 is for a circular aperture 24 and circular gel 30, with the data therefor being shown in Table 1.

The present invention provides a system for providing a comfortable transition between stimulated and non-stimulated areas on the body 34, thus allowing patients to tolerate higher voltages and currents which often results in more efficient therapeutic effects.

The medical electrode system 10 in accordance with the present invention is utilized by first adhering the gel pad 30 to the facing material 16 and over the patch 14 and thereafter coupling the patches to the body part 34. For compressive application, the system 70 is utilized with the strap 76, 78 providing compressional application of the medical electrode system onto the body part 34.

Although there is described hereinabove a specific arrangement of a medical electrode system in accordance with the present invention for the purpose of illustrating the manner in which the invention can be used to advantage, it will be appreciated that the invention is not limited thereto. Accordingly, any and all variations and modifications which may occur to those skilled in the art are to be considered to be within the scope and spirit of the invention as defined in the appended claims.

What is claimed is:

1. A medical electrode system comprising:

TABLE 1

| 16 × 40 Pad Test Array | | A/D Gain: | 8 |
|---|---|---|---|
| Phase Duration of Stimulus: | 200 μSec | Phase Amplitude: | 50 mA |
| Valid Stimulus Threshold: | 0.03 VDC | Maximum Impedance Displayed: | 5000 Ohm/cm$^2$ |
| Electrode Information: | | A/D Sample Rate: | 100000 Hz |
| Description: | 50 mm Dia. | | |
| Current Distribution Media: | Woven | Surface Area: | 20.27 (cm$^2$) |
| Connector: | Wire | Conductive Gel: | Promeon |
| Average Impedance/cm$^2$ | 166.17 Ohm | Lead Length: | 4 in |
| Average Total Impedance (Average Impedance/Surface Area): | | | 8.308 Ohm |
| Total Impedance (Kirchhoff's 2nd Law): | | | 0.551 Ohm |

| Array Dots Row | 16 | 15 | 14 | 13 | 12 | 11 | 10 | 9 | 8 | 7 | 6 | 5 | 4 | 3 | 2 | 1 (Ohm/cm$^2$): |
|---|---|---|---|---|---|---|---|---|---|---|---|---|---|---|---|---|
| Col 1 | — | — | — | — | — | 851 | 326 | 258 | 257 | 273 | 331 | 519 | — | — | — | — |
| Col 2 | — | — | — | 632 | 278 | 210 | 182 | 158 | 178 | 194 | 200 | 226 | 303 | — | — | — |
| Col 3 | — | — | 412 | 227 | 185 | 133 | 129 | 101 | 129 | 123 | 139 | 154 | 191 | 256 | 571 | — |
| Col 4 | — | 504 | 232 | 149 | 185 | 93 | 100 | 102 | 97 | 81 | 81 | 102 | 150 | 182 | 219 | 51 |
| Col 5 | — | 308 | 164 | 103 | 90 | 78 | 90 | 72 | 82 | 80 | 79 | 83 | ill | 151 | 184 | 254 |
| Col 6 | 617 | 246 | 148 | 90 | 82 | 74 | 73 | 70 | 81 | 77 | 90 | 82 | 91 | 124 | 154 | 201 |
| Col 7 | 380 | 215 | 127 | 85 | 79 | 76 | 78 | 76 | 79 | 78 | 46 | 79 | 85 | 114 | 50 | 183 |
| Col 8 | 342 | 196 | 108 | 84 | 84 | 76 | 79 | 77 | 102 | 80 | 78 | 78 | 79 | 116 | 50 | 181 |
| Col 9 | 350 | 193 | 111 | 80 | 86 | 81 | 79 | 78 | 80 | 75 | 74 | 78 | 84 | 122 | 152 | 190 |
| Col 10 | 442 | 212 | 132 | 91 | 87 | 82 | 77 | 77 | 75 | 74 | 73 | 77 | 101 | IZ9 | 149 | 197 |
| Col 11 | — | 241 | 159 | 106 | 79 | 77 | 77 | 75 | 75 | 75 | 74 | 75 | ill | 132 | 52 | 211 |
| Col 12 | — | 333 | 191 | 146 | 98 | 76 | 78 | 73 | 71 | 73 | 73 | 88 | 126 | 148 | 204 | 312 |
| Col 13 | — | — | 252 | 184 | 135 | 94 | 83 | 76 | 78 | 79 | 99 | 128 | 153 | 178 | 225 | 543 |
| Col 14 | — | — | 633 | 240 | 181 | 147 | 129 | 19 | 122 | 131 | 146 | 169 | 193 | 226 | 341 | — |
| Col 15 | — | — | — | — | 296 | 218 | 183 | 172 | 175 | 181 | 191 | 220 | 260 | 390 | — | — |
| Col 16 | — | — | — | 446 | 298 | 258 | 261 | 298 | 435 | — | — | — | — | — | — | — | a washable electrically non-conductive backing material;

a washable flexible, electrically conductive patch disposed on the backing material;

a lead wire electrically connected to the patch;

2. The medical electrode system according to claim 1, further comprising means, defining a shape of the patch, aperture and gel means, for tailoring a current distribution through the gel means.

3. The medical electrode system according to claim 1, wherein the backing material and facing material are fabric.

4. The medical electrode system according to claim 3, wherein the backing material and facing material comprise a woven fabric with a weave enabling visual acuity therethrough sufficient to facilitate placement of the backing material unto the body part.

5. The medical electrode system according to claim 1, further comprising a moisture barrier disposed between the patch and the backing material.

6. A medical electrode system comprising:
an electrically non-conductive backing material;
a flexible, electrically conductive patch disposed on the backing material;
a lead wire electrically connected to the patch;
an electrically non-conductive facing material disposed over the patch, the facing material including means, defining an aperture therein, for exposing a portion of the patch, said aperture having a maximum dimension smaller than a minimum dimension of the patch;
separate and disposable electrically conductive gel means for releasably coupling the patch to a body part, said separate and disposable electrically conductive gel means having a minimum dimension smaller than the aperture maximum dimension and formed from a material enabling the gel means to be removed, intact, from said body part and patch; and
means, defining a shape of the patch, aperture and gel means, for tailoring a current distribution through the gel means, said patch aperture and gel means being of the same geometrical shape.

7. A medical electrode system comprising:
an electrically non-conductive backing material;
a plurality of flexible, electrically conductive patches disposed on the backing material;
a separate lead wire electrically connected to each of the patches;
an electrically non-conductive facing material disposed over the patches, the facing material including means, defining a plurality of apertures therein, for exposing a portion of each patch, each aperture having a maximum dimension smaller than a minimum dimension of each patch;
a plurality of separate and disposable electrically conductive gel means, for releasably coupling the patches to a body part, each gel means having a different conductivity and each gel means having a minimum dimension larger than the aperture maximum dimension and formed from a material enabling the gel means to be removed, intact, from a said body part and patches;
means, defining a shape of each patch, aperture and gel means, for tailoring a current distribution through each gel means, each patch, aperture and gel means being of the same geometrical shape.

8. The medical electrode system according to claim 7, wherein the backing material comprises means, defining an opening therein, for facilitating placement of the backing material onto a body part by visually observing the body part through the opening.

9. A medical electrode system comprising:
an electrically non-conductive backing material;
a plurality of electrically conductive patches disposed on the backing material;
a lead wire separate electrically connected to each of the patches; and
a plurality of separate electrically conductive gel means for both releasably coupling the patches to a body part and for iontophoretically delivering a drug into the body part, said drug being disposed in said separate electrically conductive gel means and the gel means being formed from a material enabling the gel means to be removed, intact, from said body part and patches, each gel means having a different conductivity.

10. The medical electrode system according to claim 9, further comprising an electrically non-conductive facing material disposed over the patches, the facing material including means, defining a plurality of apertures therein, for exposing a portion of each of the patches, each said aperture having a maximum dimension smaller than a minimum dimension of each patch.

11. The medical electrode system according to claim 10 further comprising means, defining a shape of patch, aperture and gel means, for tailoring a current distribution through each gel means.

12. The medical electrode system according to claim 10 wherein the backing material and facing material are fabric.

13. The medical electrode system according to claim 12 wherein the backing material and facing material comprise a woven fabric with a weave enabling visual acuity therethrough sufficient to facilitate placement of the backing material onto the body part.

14. The medical electrode system according to claim 9 further comprising non-electrical means for controlling an amount of drug released from the gel means.

15. The medical electrode system according to claim 14 wherein the non-electrical means for controlling drug release from the gel means comprises an electrically non-conductive facing material disposed over the patches, the facing material defining a plurality of apertures therein, for exposing selected areas of the patches to the gel means.

16. The medical electrode system according to claim 9 wherein the backing material is continuous.

17. The medical electrode system according to claim 16 wherein the backing material comprises means, defining an opening therein, for facilitating placement of the backing material on a body part by visually observing the body part through the opening.

18. A medical electrode system comprising:
an electrically non-conductive backing material;
a plurality of flexible electrically conductive patches disposed on the backing material in a selected array, the array being selected for enabling coordinated placement of the patches on a selected body part;
an electrically non-conductive facing material disposed over the patches, the facing material including means, defining a plurality of apertures therein and disposed in the selected array, for exposing a portion of each patch, said apertures each having a maximum dimension smaller than a minimum dimension of a corresponding patch;

lead wires electrically connected to each patch;

separate and disposable conductive gel means for releasably coupling the patches to a body part, the gel means being formed from a material enabling the gel means to be removed, intact, from said body part and patch; and means, defining a shape of the patch, aperture and gel means, for tailoring a current distribution through the gel means.

19. The medical electrode system according to claim 18 wherein the gel means comprises a plurality of individual gel patches, each sized to cover one of the apertures.

20. The medical electrode system according to claim 18 wherein the patches, apertures and gel means are of the same geometrical shape.

21. The medical electrode system according to claim 18 wherein the patched, apertures and gel means are of different geometrical shape.

22. The medical electrode system according to claim 18 wherein the backing material is continuous.

23. The medical electrode system according to claim 22 wherein the backing material comprises means, defining an opening therein, for facilitating placement of the backing material onto a body part by visually observing the body part through the opening.

24. The medical electrode system according to claim 18 wherein the backing material and facing material are fabric.

25. The medical electrode system according to claim 24 wherein the backing material and facing material comprises a woven fabric with a weave enabling visual acuity therethrough sufficient to facilitate placement of the backing material onto the body part.

26. A medical electrode system comprising:

an electrically non-conductive backing material;

a plurality of flexible, electrically conductive patches disposed on the backing material;

a separate lead wire electrically connected to each patch;

a plurality of separate electrically conductive gel means for releasably coupling the patches to a body part, the gel means being formed from a material enabling the gel means to be removed, intact, from said body part and patches, each gel means having a different conductivity; and means for controlling current distribution provided to the body part from the patches through the gel means, said means for controlling current distribution comprising an electrically non-conductive facing material disposed over the patches and including apertures therein having maximum dimensions smaller than a minimum dimension of the patches and smaller than a minimum dimension of the gel means.

27. The medical electrode system according to claim 26 wherein the backing material and facing material are fabric.

28. The medical electrode system according to claim 27 wherein the backing material and facing material comprise a woven fabric with a weave enabling visual acuity therethrough sufficient to facilitate placement of the backing material onto the body part.

29. The medical electrode system according to claim 26 further comprising a moisture barrier disposed between the patches and the backing material.

* * * * *

UNITED STATES PATENT AND TRADEMARK OFFICE
CERTIFICATE OF CORRECTION

PATENT NO. : 5,450,845
DATED : September 19, 1995
INVENTOR(S) : Jens Axelgaard

It is certified that error appears in the above—identified patent and that said Letters Patent is hereby corrected as shown below:

Claim 1 should read as follows:

1. A medical electrode system comprising:

a washable electrically non-conductive backing material;

a washable flexible, electrically conductive patch disposed on the backing material;

a lead wire electrically connected to the patch;

an electrically non-conductive facing material disposed over the patch, the facing material including means, defining an aperture therein, for exposing a portion of the patch, said aperture having a maximum dimension smaller than a minimum dimension of the patch; and

UNITED STATES PATENT AND TRADEMARK OFFICE
CERTIFICATE OF CORRECTION

PATENT NO. : 5,450,845
DATED : September 19, 1995
INVENTOR(S) : Jens Axelgaard

It is certified that error appears in the above-indentified patent and that said Letters Patent is hereby corrected as shown below:

separate and disposable electrically conductive gel means for releasably coupling the patch to a body part, the gel means having a minimum dimension larger than the aperture maximum dimension and formed from a material enabling the gel means to be removed, intact, from said body part and patch.

Signed and Sealed this

Tenth Day of June, 1997

*Attest:*

BRUCE LEHMAN

*Attesting Officer*     *Commissioner of Patents and Trademarks*